(12) United States Patent
Benson et al.

(10) Patent No.: US 11,298,162 B2
(45) Date of Patent: Apr. 12, 2022

(54) LOAD SENSING ASSEMBLY FOR A SPINAL IMPLANT

(71) Applicant: Warsaw Orthopedic, Inc., Warsaw, IN (US)

(72) Inventors: Nicholas M. Benson, Collierville, TN (US); Richard L. Brown, Mesa, AZ (US); Newton H. Metcalf, Memphis, TN (US); Clark B. Norgaard, Phoenix, AZ (US); Steven D. Glassman, Louisville, KY (US); Shane Burch, San Anselmo, CA (US); Domagoj Coric, Charlotte, NC (US); Robert A Fields, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 645 days.

(21) Appl. No.: 16/039,592

(22) Filed: Jul. 19, 2018

(65) Prior Publication Data
US 2020/0022739 A1 Jan. 23, 2020

(51) Int. Cl.
*A61B 17/70* (2006.01)
*A61B 5/07* (2006.01)
(Continued)

(52) U.S. Cl.
CPC .......... *A61B 17/7074* (2013.01); *A61B 5/076* (2013.01); *A61B 5/6878* (2013.01);
(Continued)

(58) Field of Classification Search
CPC ......... A61F 2002/4666; A61B 17/7074; A61B 17/7032; A61B 17/7034;
(Continued)

(56) References Cited

U.S. PATENT DOCUMENTS 5,697,929 A 12/1997 Mellinger
6,004,349 A 12/1999 Jackson
(Continued)

FOREIGN PATENT DOCUMENTS

| WO | 2015200720 A2 | 12/2015 |
|----|---------------|---------|
| WO | 2017007821 A1 | 1/2017 |
| WO | 2017165717 A1 | 9/2017 |

OTHER PUBLICATIONS

International Search Report, PCT/US2019/042516, dated Oct. 31, 2019.
(Continued)

*Primary Examiner* — Devin B Henson
*Assistant Examiner* — H. Q. Nguyen
(74) *Attorney, Agent, or Firm* — Fox Rothschild LLP

(57) ABSTRACT

A load sensing assembly for a spinal implant includes a set screw having a central opening that extends from a first end of the set screw toward a second end of the set screw. The second end of the set screw is configured to engage with an anchoring member. The load sensing assembly includes an antenna, an integrated circuit in communication with the antenna, where the integrated circuit is positioned within the central opening of the set screw, and a strain gauge in connection with the integrated circuit. The strain gauge is located within the central opening of the set screw in proximity to the second end of the set screw.

16 Claims, 14 Drawing Sheets

(51) Int. Cl.
*A61B 5/00* (2006.01)
*A61F 2/30* (2006.01)
*A61F 2/46* (2006.01)
*A61B 5/01* (2006.01)

(52) U.S. Cl.
CPC ...... *A61B 17/7032* (2013.01); *A61B 17/7035* (2013.01); *A61F 2/4657* (2013.01); *A61B 5/0031* (2013.01); *A61B 5/01* (2013.01); *A61B 17/705* (2013.01); *A61B 17/7041* (2013.01); *A61B 17/7044* (2013.01); *A61B 17/7055* (2013.01); *A61B 17/7059* (2013.01); *A61F 2002/3067* (2013.01); *A61F 2002/4666* (2013.01)

(58) Field of Classification Search
CPC .......... A61B 2562/0261; A61B 5/4566; A61B 5/4851; A61B 5/6878; A61B 5/0031; A61B 5/076; A61B 2090/064–065; A61B 2017/0425; A61B 2017/044; A61B 2017/0453; A61B 17/686; A61B 17/7082; A61B 17/7083; A61B 17/7085; A61B 17/7086; A61B 17/7088; A61B 17/7089; A61B 17/7091; A61B 17/7092; A61B 17/7001; A61B 17/7002; A61B 17/7004; A61B 17/7005; A61B 17/7007; A61B 17/7008; A61B 17/701; A61B 17/7011; A61B 17/7013; A61B 17/7014; A61B 17/7019; A61B 17/702; A61B 17/7035; A61B 17/7037; A61B 17/7038; A61B 17/704; A61B 17/7041; A61B 17/7043; A61B 17/7044; A61B 17/7046; A61B 17/7058; F16B 35/005
See application file for complete search history.

(56) References Cited

U.S. PATENT DOCUMENTS

| | | | |
|---|---|---|---|
| 6,179,841 | B1 | 1/2001 | Jackson |
| 6,280,445 | B1 | 8/2001 | Morrison et al. |
| 6,485,491 | B1 | 11/2002 | Farris et al. |
| 8,057,519 | B2 | 11/2011 | Justis et al. |
| 8,868,200 | B2 | 10/2014 | Abrahamson et al. |
| 9,241,738 | B2 | 1/2016 | Quevedo et al. |
| 9,498,294 | B2 | 11/2016 | Rigsby et al. |
| 2005/0228326 | A1* | 10/2005 | Kalfas ................ A61B 17/7007 602/19 |
| 2005/0267477 | A1 | 12/2005 | Jackson |
| 2006/0052782 | A1* | 3/2006 | Morgan ................ A61B 90/06 606/60 |
| 2008/0281212 | A1 | 11/2008 | Nunez et al. |
| 2009/0234391 | A1 | 9/2009 | Butler et al. |
| 2010/0201118 | A1 | 8/2010 | Anton et al. |
| 2010/0298886 | A1 | 11/2010 | Kraus et al. |
| 2011/0106179 | A1 | 5/2011 | Prevost et al. |
| 2011/0319755 | A1* | 12/2011 | Stein ..................... A61F 2/4657 600/437 |
| 2017/0196508 | A1* | 7/2017 | Hunter ................... A61B 17/70 |
| 2018/0195547 | A1* | 7/2018 | Demeocq ................ F16B 31/02 |
| 2019/0038214 | A1* | 2/2019 | Mikhail ................. G01R 27/02 |

OTHER PUBLICATIONS

International Search Report, PCT/US2019/042511, dated Oct. 31, 2019.

International Search Report and Written Opinion, PCT/US2020/041487 dated Nov. 2, 2020.

* cited by examiner

LOAD SENSING ASSEMBLY FOR A SPINAL IMPLANT

TECHNICAL FIELD

The present disclosure generally relates to load sensing assemblies for implant devices, and more particularly to load sensing assemblies for implant devices that are used to treat various spinal disorders.

BACKGROUND

Treatment of spinal disorders, such as degenerative disc disease, disc herniations, scoliosis or other curvature abnormalities, and fractures, often requires surgical treatments. For example, spinal fusion may be used to limit motion between vertebral members. As another example, implants may be used to preserve motion between vertebral members.

Surgical treatment typically involves the use of longitudinal members, such as spinal rods. Longitudinal members may be attached to the exterior of two or more vertebral members to assist with the treatment of a spinal disorder. Longitudinal members may provide a stable, rigid column that helps bones to fuse, and may redirect stresses over a wider area away from a damaged or defective region. Also, rigid longitudinal members may help in spinal alignment.

Screw assemblies may be used to connect a longitudinal member to a vertebral member. A screw assembly may include a pedicle screw, hook, or other connector and/or a set screw, among other components. A pedicle screw can be placed in, above and/or below vertebral members that were fused, and a longitudinal member can be used to connect the pedicle screws which inhibits or controls movement. A set screw can be used to secure the connection of a longitudinal member and a pedicle screw, hook or other connector. However, the connection force and continued integrity of the connection between a longitudinal member and a pedicle screw or other connector can be challenging to monitor during and after implantation. In addition, it is difficult to monitor that a proper or acceptable or any force is maintained between a set screw and a longitudinal member.

SUMMARY

In an embodiment, a load sensing assembly for a spinal implant includes a set screw having a central opening that extends from a first end of the set screw toward a second end of the set screw. The second end of the set screw is configured to engage with an anchoring member. The load sensing assembly includes an antenna, an integrated circuit in communication with the antenna, where the integrated circuit is positioned within the central opening of the set screw, and a strain gauge in connection with the integrated circuit. The strain gauge is located within the central opening of the set screw in proximity to the second end of the set screw.

In an embodiment, the antenna may include an opening there through, where the antenna circumferentially surrounds at least a portion of the set screw. Alternatively, at least a portion of the antenna may be positioned in the central opening of the set screw.

The load sensing assembly may include an electronics component having a top surface, a bottom surface, and one or more electrical circuits. The integrated circuit may be positioned on the top surface of the electronics component. The strain gauge may be operably connected to the bottom surface of the electronics component.

In an embodiment, the strain gauge may be configured to measure a force between the set screw and a longitudinal member when the set screw is engaged with the anchoring member.

The integrated circuit may include memory, and the integrated circuit may be configured to store one or more measurements made by the strain gauge in the memory, and transmit the one or more measurements to a reader when the reader is in proximity to the integrated circuit.

In an embodiment, the integrated circuit may include memory, and the integrated circuit may be configured to store a unique identifier associated with the set screw in the memory, and transmit the unique identifier to a reader when the reader is in proximity to the integrated circuit.

In an embodiment, the load sensing assembly may include an anchoring member having a channel that is configured to receive a longitudinal member and a second strain gauge located within the channel. The second strain gauge may be configured to measure a force between the anchoring member and the longitudinal member when positioned in the channel.

In various embodiments, the integrated circuit may include one or more of the following radio frequency identification (RFID) chip, or a near-field communication (NFC) chip.

In an embodiment, a load sensing assembly for a spinal implant includes an anchoring member having a head and a base. The head includes a channel that is configured to receive a longitudinal member, and one or more head openings that extend from an external portion of the head into the channel. The load sensing assembly includes an antenna having an opening there through, wherein the antenna circumferentially surrounds at least a portion of the base of the anchoring member, and an integrated circuit in communication with the antenna, where the integrated circuit is positioned within the channel via at least one of the head openings. The load sensing assembly includes a strain gauge located within the channel, where the strain gauge is configured to measure a force between the anchoring member and the longitudinal member when positioned in the channel.

Optionally, the load sensing assembly may include an electronics component having one or more electrical circuits. The integrated circuit may be connected to the electronics component. The strain gauge may be operably connected to the electronics component via a connecting member.

In an embodiment, the integrated circuit may include memory, and the integrated circuit may be configured to store one or more measurements made by the strain gauge in the memory, and transmit the one or more measurements to a reader when the reader is in proximity to the integrated circuit.

In an embodiment, the integrated circuit may include memory, and the integrated circuit may be configured to store a unique identifier associated with the anchoring member in the memory, and transmit the unique identifier to a reader when the reader is in proximity to the integrated circuit.

A load sensing assembly may further include a set screw having a central opening that extends from a first end of the set screw toward a second end of the set screw, where the second end of the set screw may be configured to engage with the anchoring member, and a second strain gauge located within the central opening of the set screw in proximity to the second end of the set screw.

In an embodiment, the integrated circuit may include one or more of the following radio frequency identification (RFID) chip, or a near-field communication (NFC) chip.

In an embodiment, a load sensing assembly for a spinal implant includes an antenna, an electronics component having one or more electrical circuits that is operably connected to the antenna, an integrated circuit operably connected to at least a portion of the electronics component, and a strain gauge in communication with the integrated circuit, where the strain gauge is configured to measure a force between the implant and a longitudinal member.

The electronics component may be operably connected to the antenna via a connecting member that extends perpendicularly to the antenna. The antenna may include a radio frequency identification coil, and the antenna may be configured to circumferentially surround at least a portion of a set screw or a pedicle screw.

In an embodiment, at least a portion of the antenna may be positioned in a central opening of a set screw.

In an embodiment, the integrated circuit may include memory, and the integrated circuit may be configured to store one or more measurements made by the strain gauge in the memory, and transmit the one or more measurements to a reader when the reader is in proximity to the integrated circuit.

The integrated circuit may include memory, and the integrated circuit may be configured to store a unique identifier associated with the implant in the memory, and transmit the unique identifier to a reader when the reader is in proximity to the integrated circuit.

DETAILED DESCRIPTION

Figure 1:
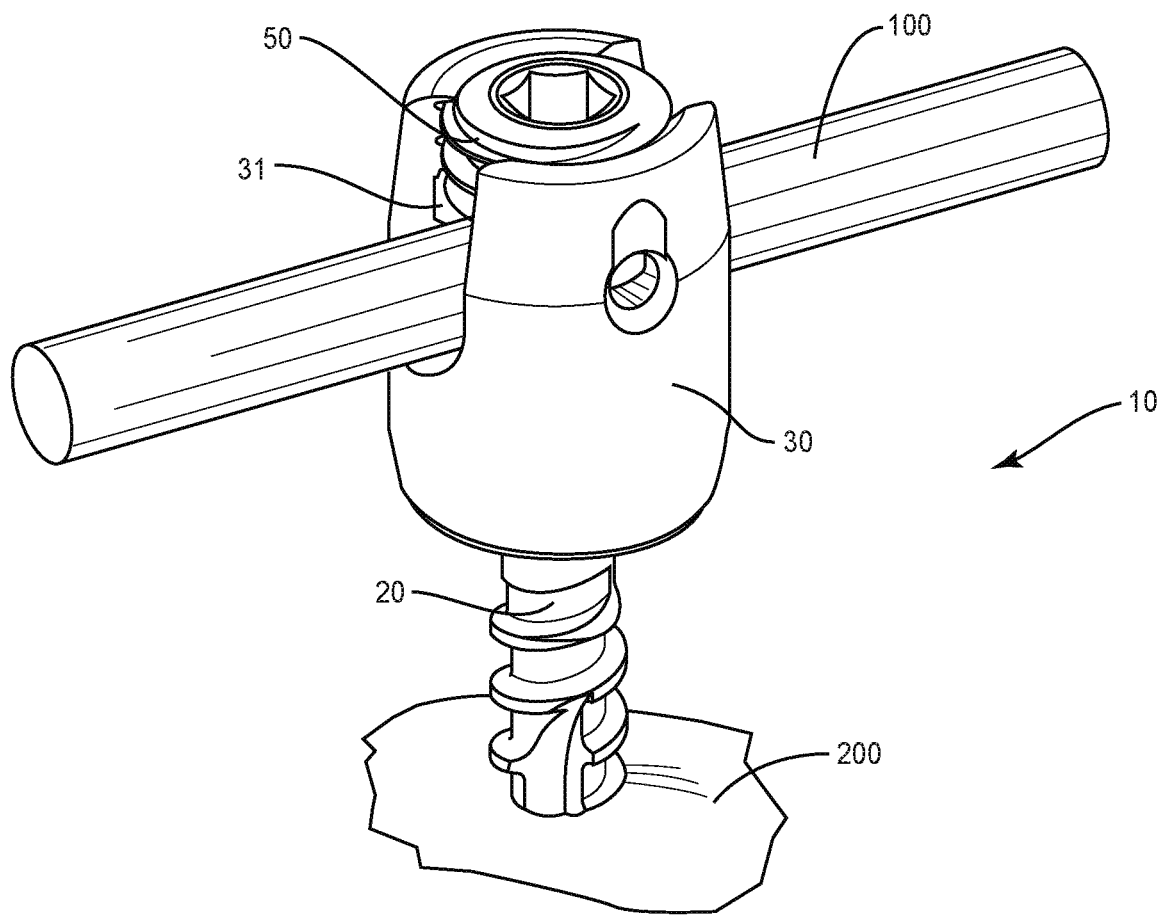
FIG. 1 illustrates an example anchoring assembly and longitudinal member according to an embodiment.

The exemplary embodiments of the surgical system and related methods of use disclosed are discussed in terms of medical devices for the treatment of musculoskeletal disorders and more particularly, in terms of a vertebral fixation screws, including for example pedicle screws, as well as hooks, cross connectors, offset connectors and related systems for use during various spinal procedures or other orthopedic procedures and that may be used in conjunction with other devices and instruments related to spinal treatment, such as rods, wires, plates, intervertebral implants, and other spinal or orthopedic implants, insertion instruments, specialized instruments such as, for example, delivery devices (including various types of cannula) for the delivery of these various spinal or other implants to the vertebra or other areas within a patient in various directions, and/or a method or methods for treating a spine, such as open procedures, mini-open procedures, or minimally invasive procedures. Exemplary prior art devices that may be modified to include the various embodiments of load sensing systems include, for example, U.S. Pat. Nos. 6,485,491 and 8,057,519, all incorporated herein by reference in their entirety.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting.

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following discussion includes a description of a vertebral pedicle screw system and related components and methods of employing the vertebral pedicle screw in accordance with the principles of the present disclosure. Reference is made in detail to the exemplary embodiments of the present disclosure, which are illustrated in the accompanying figures.

The components of the vertebral pedicle screw system described herein can be fabricated from biologically acceptable materials suitable for medical applications, including metals, synthetic polymers, ceramics and bone material and/or their composites. For example, the components of the vertebral pedicle screw system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the vertebral pedicle screw system may be formed or constructed material composites, including the above materials, to achieve various desired characteristics such as strength, rigidity, elasticity, compliance, biomechanical performance, durability and radiolucency or imaging preference. The components of the present vertebral pedicle screw system, individually or collectively, may also be fabricated from a heterogeneous material such as a combination of two or more of the above-described materials. The components of the vertebral pedicle screw system may be monolithically formed, integrally connected or include fastening elements and/or instruments, as described herein. The components of the vertebral pedicle screw system may be formed using a variety of subtractive and additive manufacturing techniques, including, but not limited to machining, milling, extruding, molding, 3D-printing, sintering, coating, vapor deposition, and laser/beam melting. Furthermore, various components of the vertebral pedicle screw system may be coated or treated with a variety of additives or coatings to improve biocompatibility, bone growth promotion or other features. To the extent the plate is entirely or partially radiolucent, it may further include radiographic markers made, for example of metallic pins, at one or both ends, on each corner of the ends, and/or along the length of the implant in various locations including near the center of the assembly.

The vertebral pedicle screw system may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the vertebral pedicle screw system may be employed with surgical procedures, as described herein, and/or, for example, discectomy, corpectomy, fusion and/or fixation treatments that employ spinal implants to restore the mechanical support function of vertebrae. In some embodiments, the pedicle screw system may be employed with surgical approaches, including but not limited to: anterior lumbar interbody fusion (ALIF), direct lateral interbody fusion (DLIF), oblique lateral lumbar interbody fusion (OLLIF), oblique lateral interbody fusion (OLIF), various types of anterior fusion procedures, and any fusion procedure in any portion of the spinal column (sacral, lumbar, thoracic, and cervical, for example).

FIG. 1 illustrates an example anchoring assembly and longitudinal member according to an embodiment. As illustrated in FIG. 1, an anchoring assembly includes a screw 20 and an anchoring member 30. The screw 20 has an elongated shape with a first end mounted within a vertebral member 200 and a second end extending outward above the vertebral member 200. The anchoring member 30 is configured to operatively connect to the second end of the screw 20 and is movably connected to the screw 20 to accommodate the longitudinal member 100 positioned at various angular positions. The anchoring member 30 includes a channel 31 sized to receive the longitudinal member 100. A set screw 50 attaches to the anchoring member 30 to capture the longitudinal member 100 within the channel 31.

Figure 2:
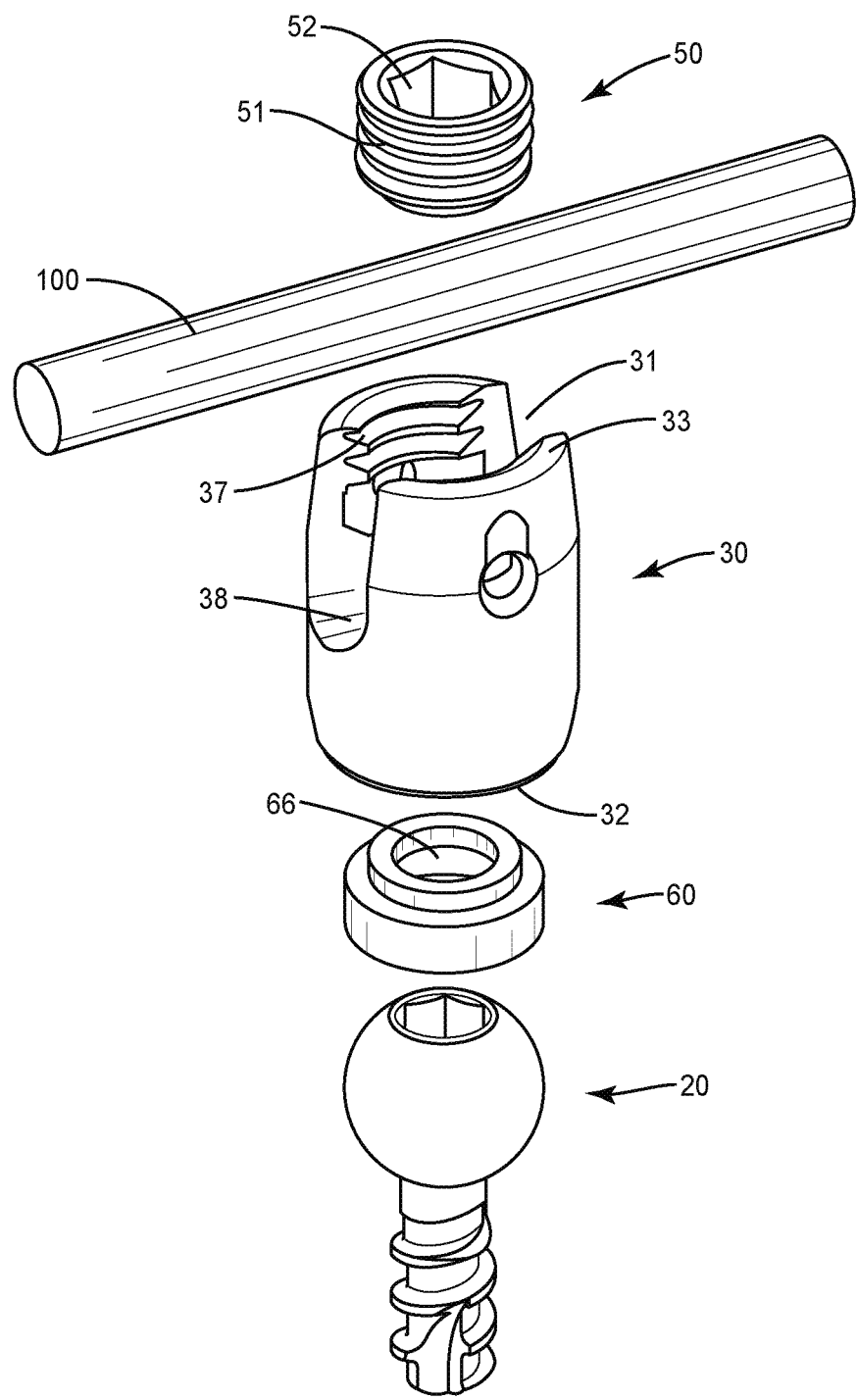
FIG. 2 illustrates an example exploded view of a screw assembly and longitudinal member according to an embodiment.

FIG. 2 illustrates an example exploded view of a screw assembly and longitudinal member according to an embodiment. As shown by FIG. 2, anchoring member 30 provides a connection between the screw 20 and longitudinal member 100. Anchoring member 30 includes a first end 32 that faces towards the vertebral member 200, and a second end 33 that faces away. A chamber is positioned between the first and second ends 32, 33 and is sized to receive at least a portion of the screw 20. In various embodiments, a first end 32 may be considered a base portion of an anchoring member 30, and a second end 33 may be considered a head portion of an anchoring member.

The second end 33 of the anchoring member 30 includes a channel 31 sized to receive the longitudinal member 100. Channel 31 terminates at a lower edge 38 that may include a curved shape to approximate the longitudinal member 100. Threads 37 may be positioned towards the second end 33 to engage with the set screw 50. In one embodiment as illustrated in FIG. 2, the threads 37 are positioned on the interior of the anchoring member 30 facing towards the channel 31. In another embodiment, the threads 37 may be on the exterior of the anchoring member 30. An interior of the anchoring member 30 may be open between the first and second ends 32, 33.

In various embodiments, an anchoring member 30 may include a washer 60. A washer 60 may be generally cylindrical and may have a hole 66 there through. As illustrated by FIG. 1 a washer 60 may be positioned near a first end 32 of an anchoring member 30. A screw 20 may engage with an anchoring member 30 via positioning through the hole 66 of a washer 60. A washer 60 may include recessed portions which may be configured to accommodate placement of a longitudinal member 100 therein. The use of a washer 60 in connection with an anchoring member 30 may help minimize misalignment of the longitudinal member within the anchoring member.

Figure 13A:
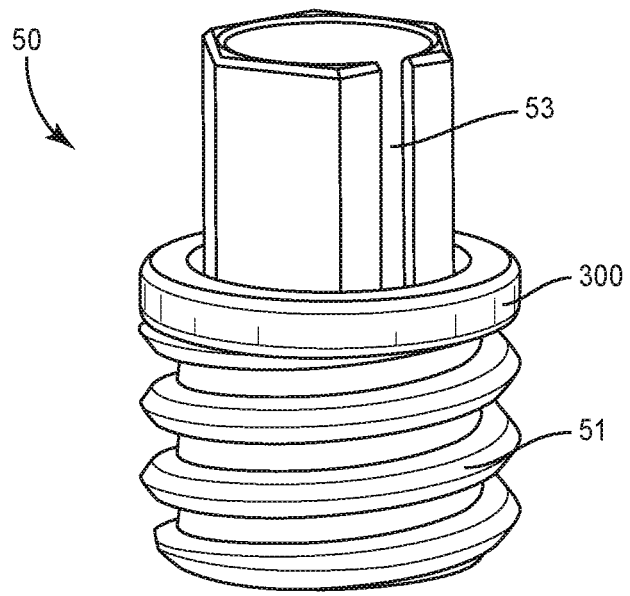
FIGS. 13A and 13B each illustrate an example set screw according to an embodiment.
Figure 13B:
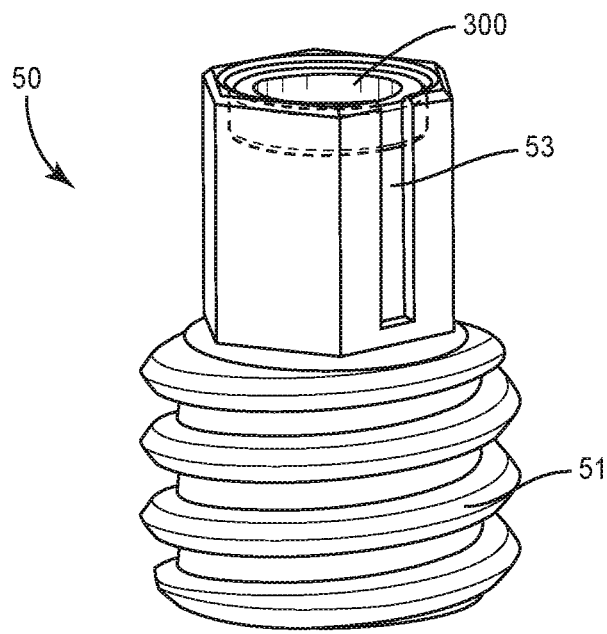

In an embodiment, set screw 50 attaches to the anchoring member 30 and captures the longitudinal member 100 within the channel 31. As illustrated in FIG. 2, the set screw 50 may be sized to fit within the interior of the channel 31 and include exterior threads 51 that engage threads 37 on the anchoring member 30. A driving feature 52 may be positioned on a top side to receive a tool during engagement with the anchoring member 30. In some embodiments, the set screw 50 may be mounted on an exterior of the anchoring member 30. Set screw 50 includes a central opening and is sized to extend around the second end 33. A set screw 50 may be a break-off set screw or a non-break-off set screw. In certain embodiments, a set screw 50 may include a slot 53 for receiving or routing of electronic connections as illustrated in FIGS. 13A and 13B. Threads 51 are positioned on an inner surface of the central opening to engage with the external threads 37 on the anchoring member 30. The set screw 50 and anchoring member 30 may be constructed for the top side of the set screw 50 to be flush with or recessed within the second end 33 when mounted with the anchoring member 30. FIG. 13A illustrates an example set screw 50 having an antenna 300 positioned on an external portion of the set screw. FIG. 13B illustrates an example set screw 50 having an antenna 300 positioned internally in a central opening of the set screw.

Figure 3:
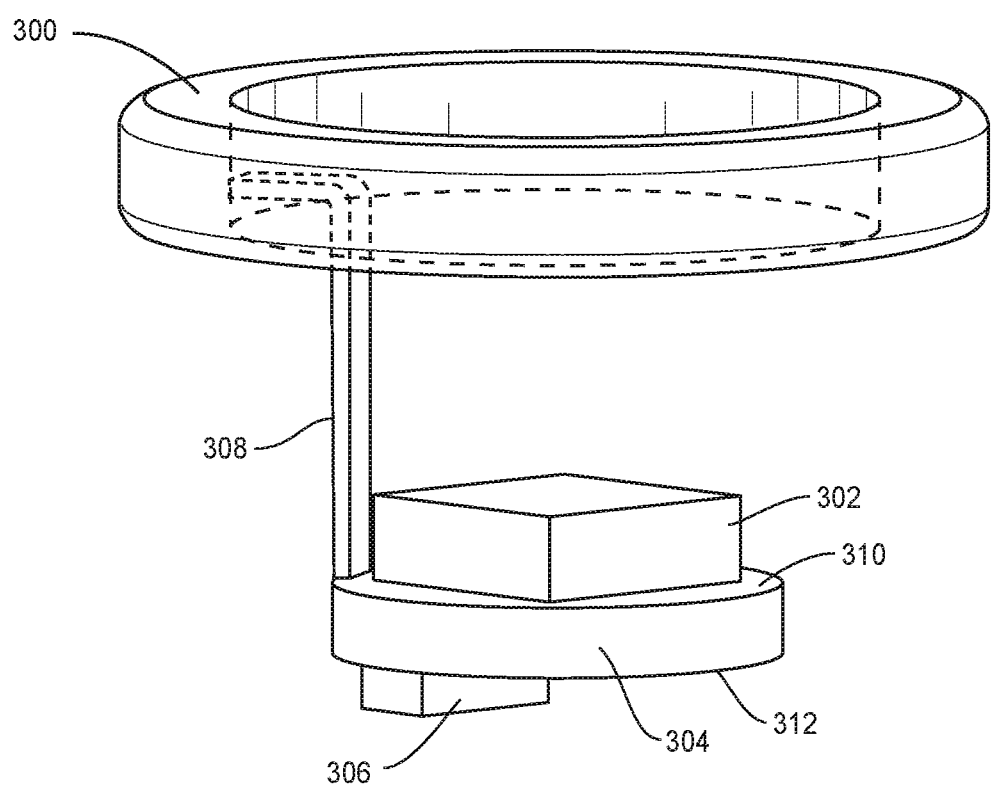
FIG. 3 illustrates an example load sensing assembly for a set screw according to an embodiment.

FIG. 3 illustrates an example load sensing assembly for a set screw according to an embodiment. As illustrated by FIG. 3, a load sensing assembly may include an antenna 300, such as a radio frequency identification (RFID) coil, a near field-communication (NFC) antenna or other short-range communication transmitter and/or receiver. A load sensing assembly may include one or more integrated circuits 302 such as, for example, an RFID chip 302 or an NFC chip. A load sensing assembly may include one or more electronics components 304 and/or a strain gauge 306, such as for example a silicon strain gauge. A strain gauge 306 may be a device that measures strain on an object. For instance, a strain gauge 306 may measure a force between a set screw and a longitudinal member when the set screw is engaged with an anchoring member. A strain gauge 306 may include one or more sensors or sensor nodes that measure strain, force, resistance, load and or the like.

In an embodiment, one or more of the electronics components may 304 include a flexible electronics component, such as, for example, a flex circuit or one or more electrical circuits. The antenna 300 may be operably connected to the electronics component 304 via a connecting member 308. For instance, as shown in FIG. 3, the connecting member 308 may be connected to both the antenna 300 and the electronics component 304. The connecting member 308 may be positioned perpendicularly to both the antenna 300 and the electronics component 304. In various embodiments, a connecting member 308 and an antenna 300 and/or electronics component 304 may be constructed integrally or may be separately constructed and attached together in any suitable manner, such as for example by adhesive, chemical, mechanical or cement bonding.

The integrated circuit 302 may be operably connected to the electronics component 304. For instance, as illustrated in FIG. 3, an electronics component 304 may have a top surface 310 and a bottom surface 312. An integrated circuit 302 may be positioned on the top surface 310 of an electronics component 304, and may be connected to the top surface in any suitable manner, including, for example, adhesive, chemical, mechanical or cement bonding. An integrated circuit 302 may include memory according to an embodiment. The memory may be used to store various information. For example, one or more measurements of a strain gauge 306 may be stored in memory. As another example, a unique identifier associated with a load sensing assembly, a component thereof, or a set screw may be stored in memory. Additional and/or alternate information or types of information may be stored according to this disclosure.

A strain gauge 306 may be operably connected, for example by adhesive, cement, mechanical or chemical bonding, to the electronics component 304. For instance, a strain gauge 306 may be operably connected to the electronics component 304 via the bottom surface 312 of the electronics component 304. A strain gauge 306 may be connected to the bottom surface 312 of an electronics component 304 in any suitable manner including, without limitation, via an adhesive bonding agent.

As shown in FIG. 3, an antenna 300 may have a generally curved shape. The antenna 300 may include a first end and a second end. The antenna 300 may include an opening that extends from the first end toward the second end.

Figure 4A:
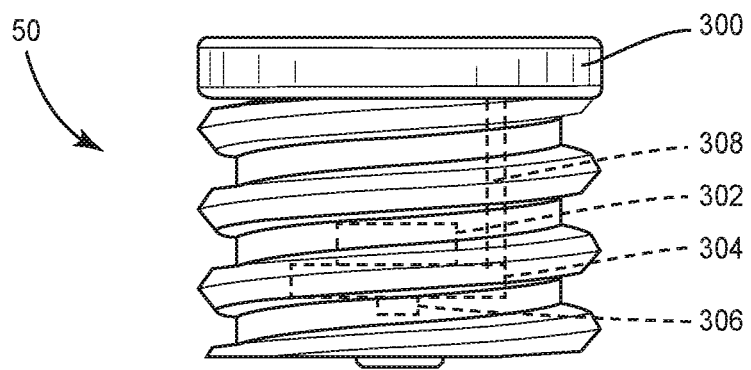
FIGS. 4A and 4B illustrates a load sensing assembly mounted to a set screw according to an embodiment.
Figure 4B:
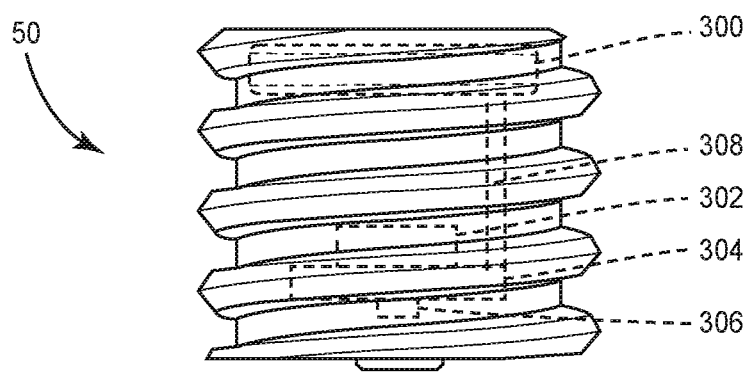

As illustrated in FIG. 4A, a load sensing assembly may be configured to be mounted to a set screw. The antenna 300 is sized to extend around the set screw such that the integrated circuit 302, electronics component 304, strain gauge 306 and connecting member 308 are positioned within the central opening of the set screw as illustrated in FIG. 4A. As illustrated in FIG. 4A, the antenna 300 may circumferentially surround at least a portion of the exterior of the set screw. In other embodiments, as illustrated by FIG. 4B, the antenna 300 may be positioned at least partially inside of the central opening of a set screw.

Figure 5:
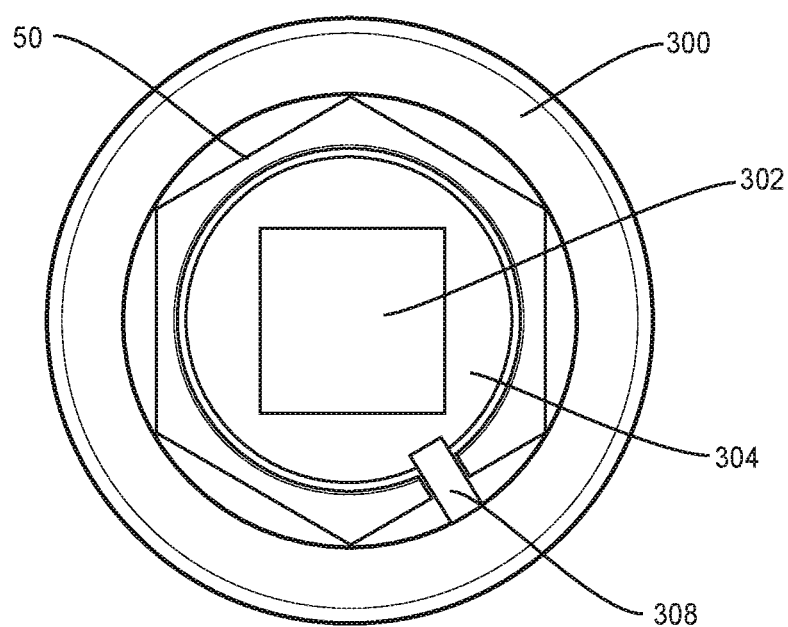
FIG. 5 illustrates a top view of a load sensing assembly mounted to a set screw according to an embodiment.

In certain embodiments, the strain gauge 306 may be connected to a portion of the central opening of the set screw in any suitable manner including, without limitation via an adhesive. The strain gauge 306 may be connected to a portion of the central opening such that it is positioned to measure a force between the set screw and a longitudinal rod when the set screw engages with an anchoring member. FIG. 5 illustrates a top view of a load sensing assembly mounted to a set screw according to an embodiment.

Figure 6:
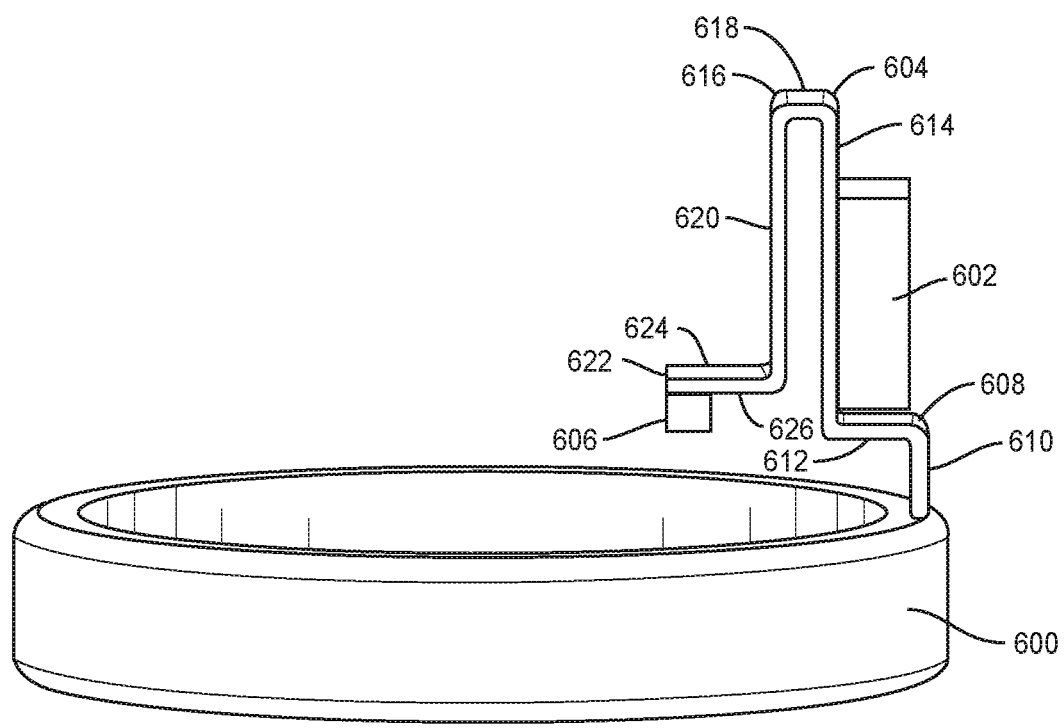
FIG. 6 illustrates an example load sensing assembly according to an embodiment.

FIG. 6 illustrates an example load sensing assembly according to an embodiment. The load sensing assembly illustrated in FIG. 6 may be mounted to an anchoring member according to various embodiments. Example anchoring members may include, without limitation screws, hooks, offset connectors, cross connectors, or other types of anchors or implants. As illustrated in FIG. 6, a load sensing assembly for an anchoring member may include an antenna 600, such as a RFID coil, an NFC antenna or other short-range communication transmitter and/or receiver. A load sensing assembly may include an integrated circuit 602, one or more electronics components 604 and/or a strain gauge 606. In an embodiment, one or more of the electronics components 604 may include a flexible electronics component, such as, for example, a flexible circuit or one or more electrical circuits.

The electronics component 604 may be connected to the antenna 600 via a connecting member 608. As shown in FIG. 6, a connecting member 608 may position an electronics component perpendicularly to the antenna 600. A connecting member 608 may include a first portion 610 that attaches to an antenna 600 and extends substantially vertically and perpendicularly from the antenna. The connecting member 608 may include a second portion 612 connected to the first portion and the electronics component. The second portion 612 may extend substantially horizontally and perpendicularly to the first portion 610. The electronics component 604 may be positioned substantially perpendicularly to the second portion 612. A connecting member 608 may be constructed integrally with an antenna 600 and/or electronics component 604, or may be separately constructed and attached together in any suitable manner.

In various embodiments, the integrated circuit 602 may be connected to a first surface 614 of the electronics component 604 as illustrated in FIG. 6. The RFID chip 602 may be connected to a first surface 614 of an electronics component in any suitable manner. An integrated circuit 602 may include memory according to an embodiment. The memory may be used to store various information. For example, one or more measurements of a strain gauge 606 may be stored in memory. As another example, a unique identifier associated with a load sensing assembly, a component thereof, or an anchoring member may be stored in memory. Additional and/or alternate information or types of information may be stored according to this disclosure.

A strain gauge 606 may be connected to an electronics component 604 via a second connecting member 616. As illustrated in FIG. 6, a second connecting member 616 may include a first portion 618, a second portion 620 and a third portion 622. The first portion 618 may connect to the electronics component 604 and may extend substantially perpendicularly to the electronics component. The second portion 620 of the second connecting member 616 may be connected to the first portion 618 of the second connecting member and may extend substantially perpendicular thereto. The third portion 622 of the second connecting member 616 may be connected to the second portion 620 of the second connecting member, and may extend substantially perpendicular to the second portion.

Figure 7:
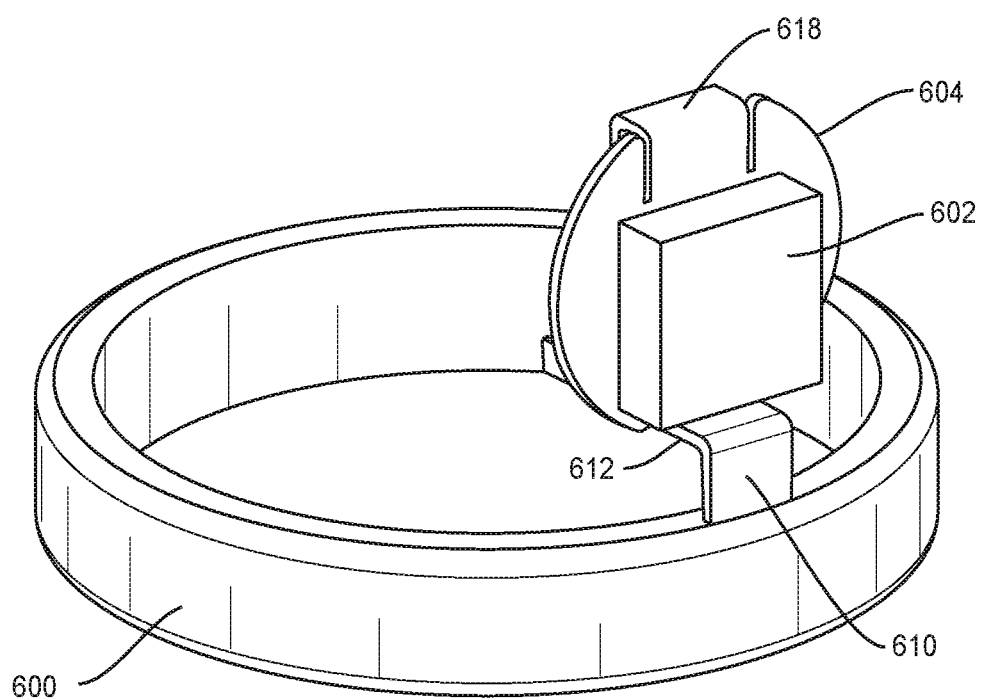
FIG. 7 illustrates a different perspective of a load sensing assembly for an anchoring member according to an embodiment.

The third portion 622 of the second connecting member 616 may have a top surface 624 and a bottom surface 626. A strain gauge 606 may be connected to the bottom surface 626 in any suitable manner. The strain gauge 606 may be configured to measure a force between the set screw and a longitudinal member. FIG. 7 illustrates a different perspective of a load sensing assembly for an anchoring member according to an embodiment.

Figure 8:
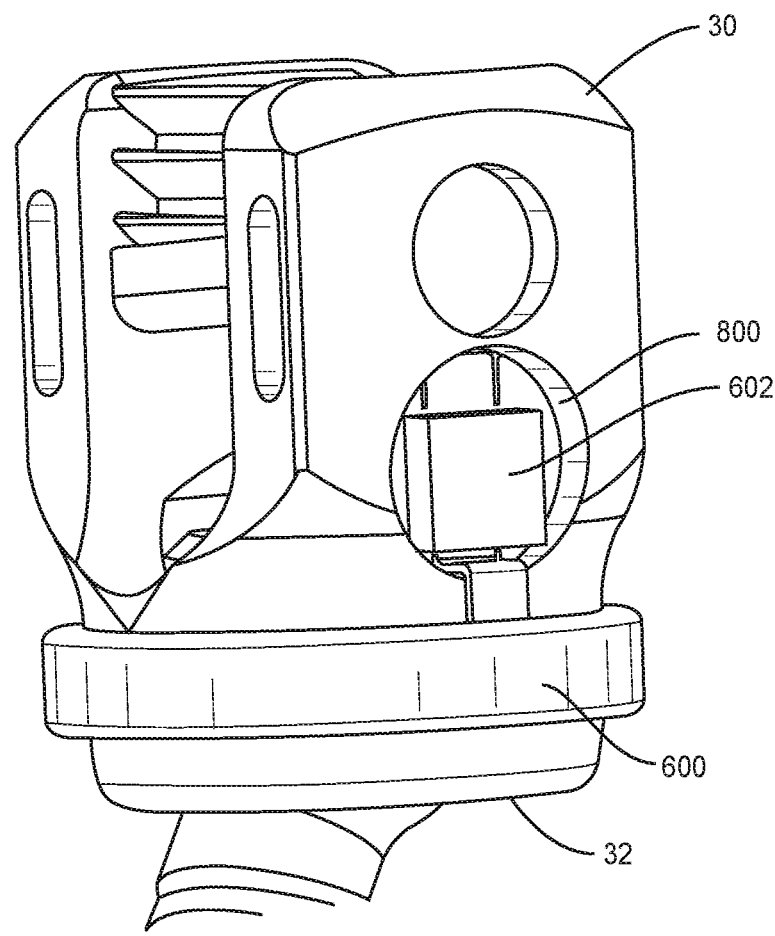
FIG. 8 illustrates a load sensing assembly connected to an anchoring member according to an embodiment.

As illustrated in FIG. 8, a load sensing assembly may be connected to an anchoring member 30. For example, a load sensing assembly may be connected to an anchoring member near a first end 32 of the anchoring member. The antenna 600 is sized to extend around the anchoring member 30, for example, near the first end 32. In various embodiments, an antenna 600 may be securely fitted around a portion of the anchoring member 30. In other embodiments, an antenna 600 may be secured to the anchoring member in any other suitable manner.

Figure 14:
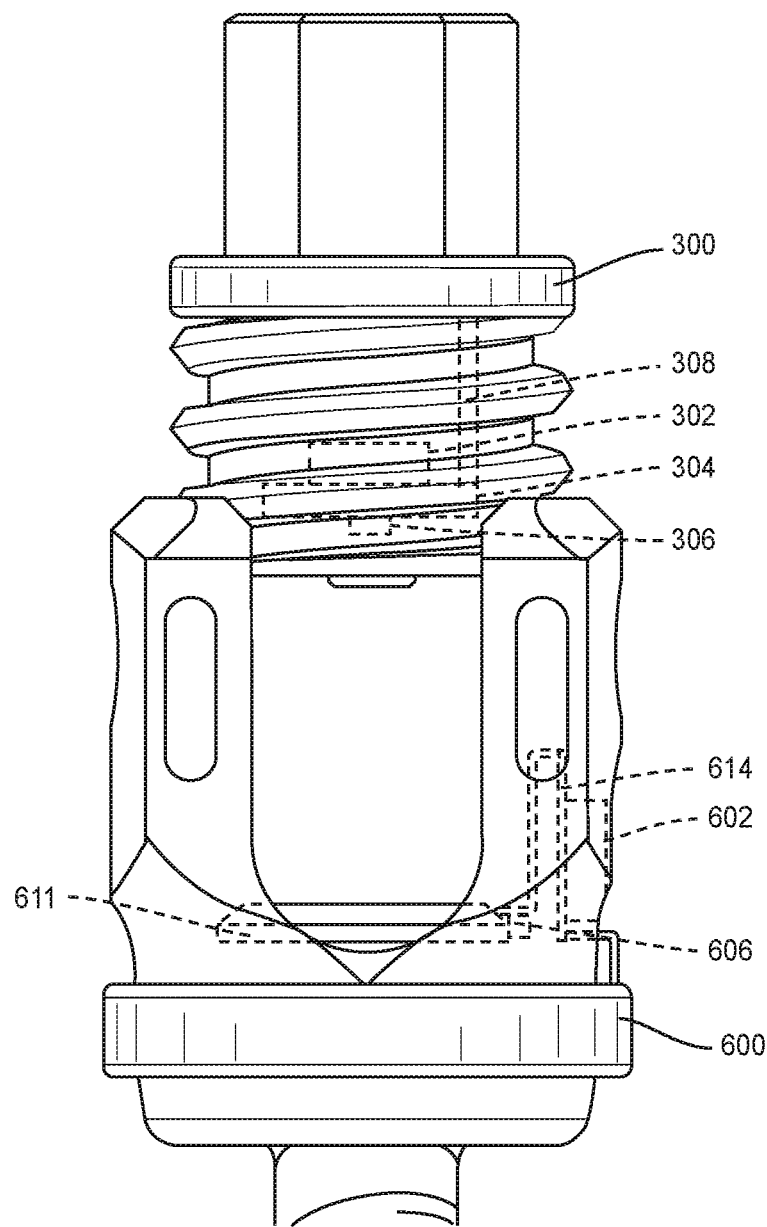
FIG. 14 illustrates an example anchoring member according to an embodiment.

The antenna 600 may be positioned on the anchoring member 30 such that the integrated circuit 602 and electronics component 604 are positioned within an opening of the anchoring member 30. For instance, as illustrated by FIG. 8, an anchoring member 30 may have one or more openings 800 that extend from an outer portion of the anchoring member into the channel 31 of the anchoring member. As illustrated by FIG. 8, the second portion of the first connecting member may extend into the opening 800 and may position the integrated circuit and/or the electronics component within the opening and/or the channel 31. Such a positioning may result in the strain gauge 606 being positioned in the channel 31 at a location where it is possible to measure a force of a longitudinal member in the channel. In an alternate embodiment, a strain gauge 606 may be positioned on or attached to a washer or pressure ring 611 within an anchoring member as illustrated by FIG. 14. In yet another embodiment, in situations where an anchoring member includes a hook member, a strain gauge 606 may be positioned on or attached to a hook portion of the hook member. Measurements obtained by the strain gauge 606 may be used to determine whether a longitudinal member is properly seated and/or torqued during and/or after implant.

Figure 9:
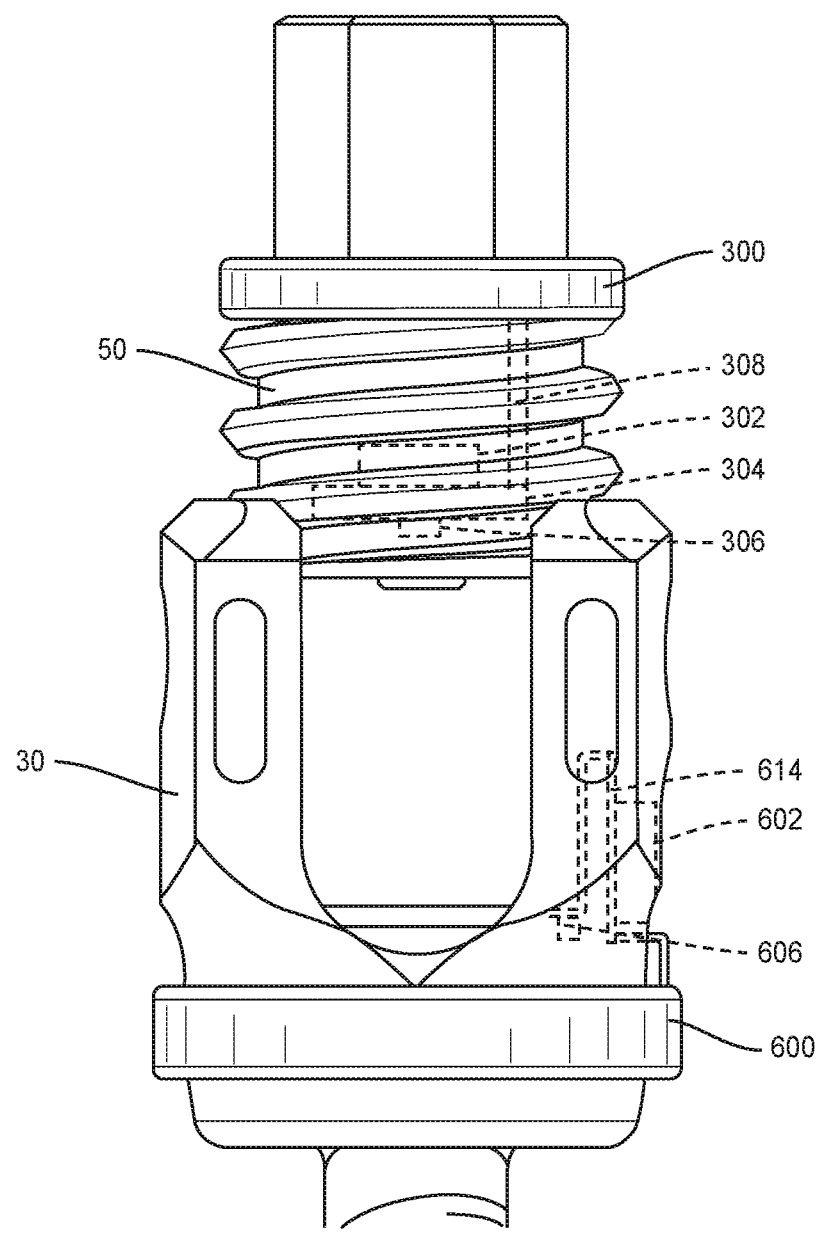
FIG. 9 illustrates a screw assembly set screw having a load sensing assembly and connected to an anchoring member that also has a load sensing assembly mounted to it according to an embodiment.
Figure 10:
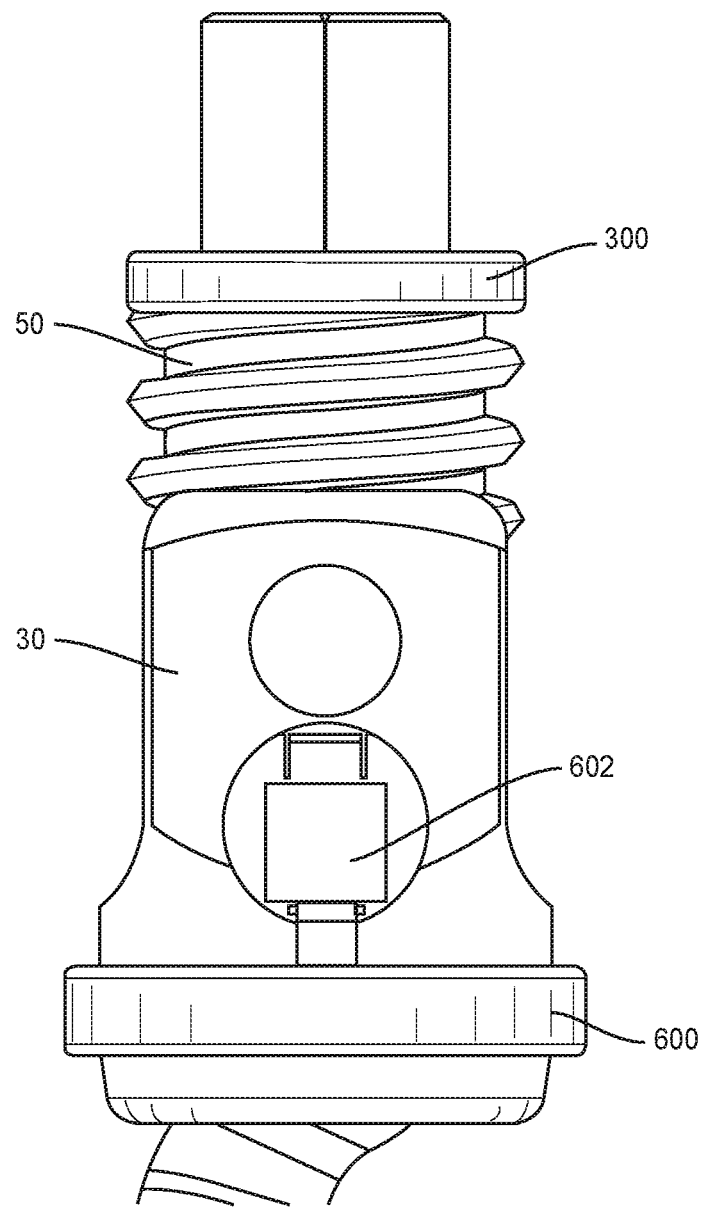
FIG. 10 illustrates a side view of the screw assembly shown in FIG. 9 according to an embodiment.
Figure 11:
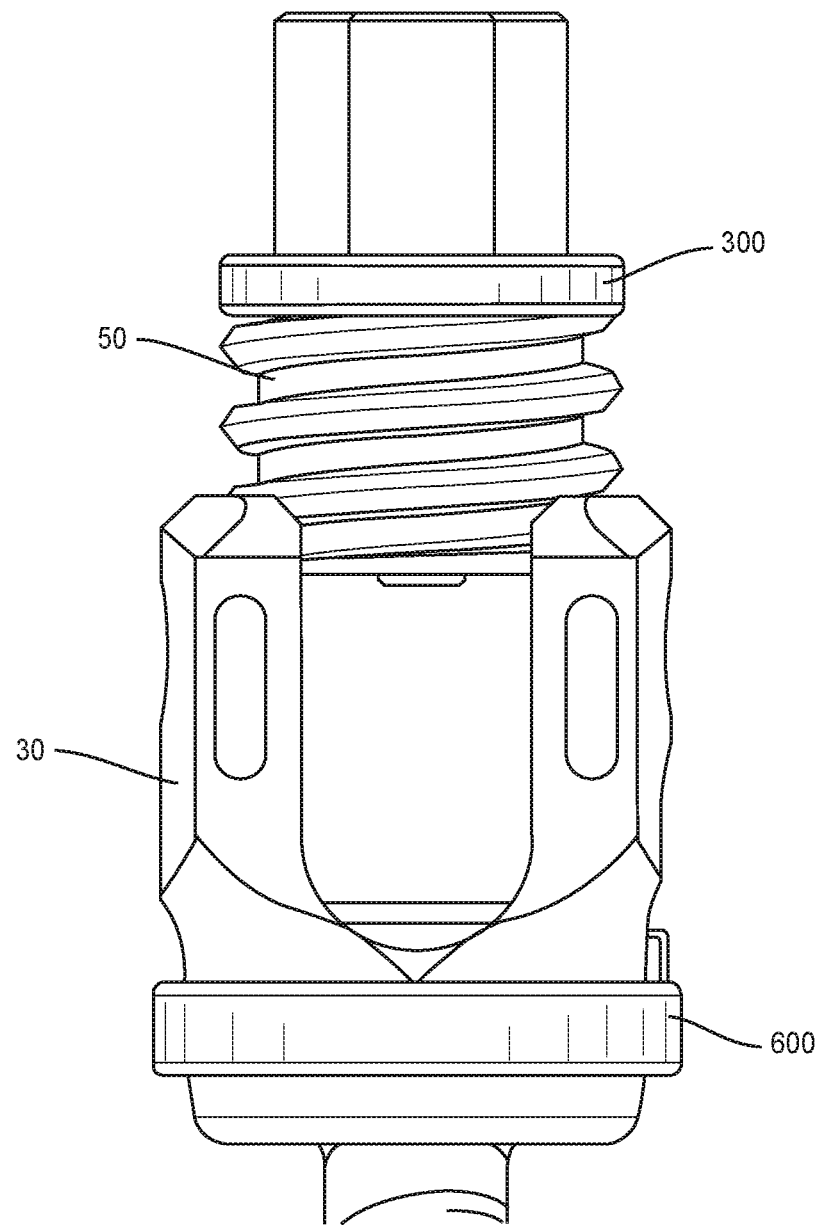
FIG. 11 illustrates a non-transparent view of the screw assembly shown in FIG. 9 according to an embodiment.

In various embodiments, a set screw having a load sensing assembly may be used with in connection with an anchoring member with or without a load, sensing assembly. FIG. 9 illustrates a set screw having a load sensing assembly engaged with an anchoring member that also has a load sensing assembly according to an embodiment. So that components of each can be clearly depicted, a longitudinal member is not shown in FIG. 9. FIG. 10 illustrates a side view of the screw assembly shown in FIG. 9 according to an embodiment. FIG. 11 illustrates a non-transparent view of the screw assembly shown in FIG. 9 according to an embodiment. Although FIGS. 9-11 illustrate an antenna located externally to a set screw, it is understood that the antenna may alternatively be located within at least a portion of the central opening of the set screw.

Figure 12:
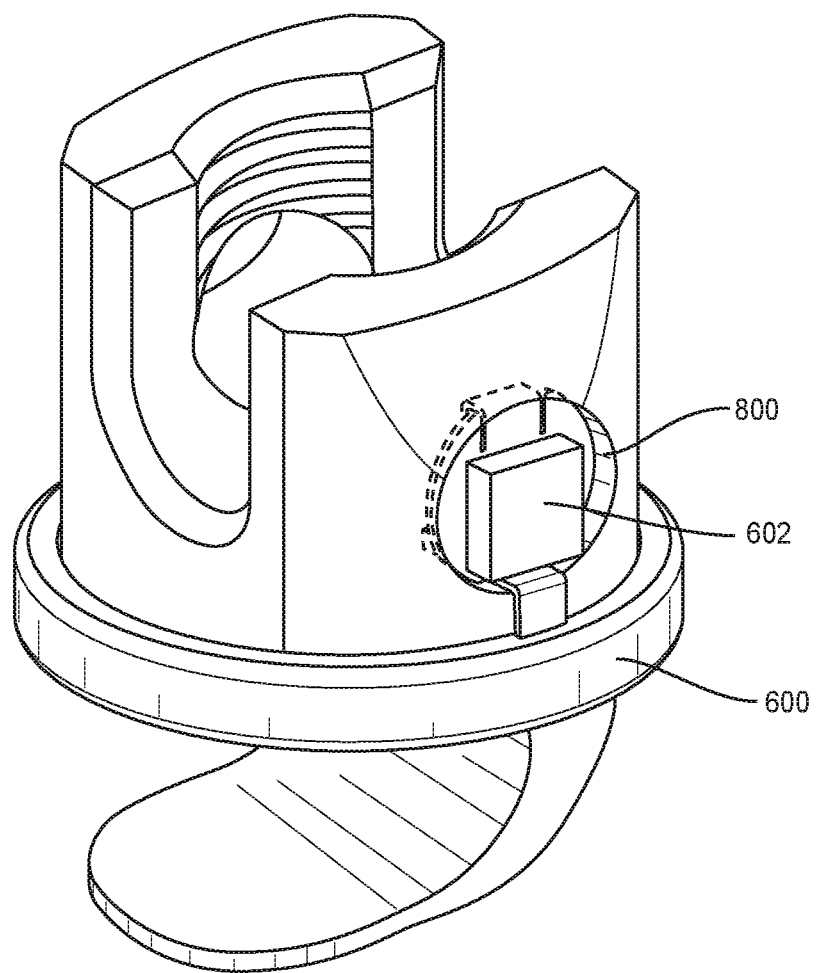
FIG. 12 illustrates an example hook member having a load sensing assembly according to an embodiment.

FIGS. 1-11 illustrate a multi-axial tulip-head pedicle screw according to various embodiments. However, it is understood that other types of anchoring members may be used within the scope of this disclosure. For example, fixed head screws or screws having differently shaped heads may be used. As another example, a hook member, a cross-link connector, an offset connector, or a hybrid hook-screw member may be used as well. FIG. 12 illustrates an example hook member having a load sensing assembly according to an embodiment.

In various embodiments, one or more measurements obtained by a strain gauge may be stored by an integrated circuit of a corresponding load sensing assembly such as, for example, in its memory. The integrated circuit may be interrogated by a reader. For instance, an RFID chip may be read by an RFID reader. As another example, an NFC chip may be read by or may otherwise communicate with an NFC reader or other NFC-enabled device. A reader may interrogate an integrated circuit when in a certain proximity to the integrated circuit. In certain embodiments, a reader may interrogate an integrated circuit that has been implanted into a patient as part of a set screw or anchoring member assembly. In other embodiments, an integrated circuit may communicate with a reader or other electronic device without being interrogated.

An integrated circuit may transmit one or more measurements to the reader. This transmission may occur in response to being interrogated by the reader, or the transmission may be initiated by the integrated circuit. The reader may receive the transmitted measurements, and may cause at least a portion of the measurements to be displayed to a user. For instance, a physician may use a reader to interrogate an RFID chip of a patient's implant. The reader may include a display, or may be in communication with a display device, which may display at least a portion of the measurements received from the RFID chip.

An integrated circuit may be passive, meaning that the chip has no internal power source and is powered by the energy transmitted from a reader. With respect to an assembly having a passive integrated circuit, the integrated circuit may not transmit information until interrogated by a reader.

In another embodiment, an integrated circuit may be active, meaning that the chip is battery-powered and capable of broadcasting its own signal. An active integrated circuit may transmit information in response to be interrogated by a reader, but also on its own without being interrogated. For instance, an active integrated circuit may broadcast a signal that contains certain information such as, for example, one or more measurements gathered by an associated strain gauge. An active integrated circuit may continuously broadcast a signal, or it may periodically broadcast a signal. Power may come from any number of sources, including, for example, thin film batteries with or without encapsulation or piezo electronics.

In various embodiments, one or more sensors of a strain gauge may transmit information by directly modulating a reflected signal, such as an RF signal. The strain gauge sensors may form a Wireless Passive Sensor Network (WPSN), which may utilize modulated backscattering (MB) as a communication technique. External power sources, such as, for example, an RF reader or other reader, may supply a WPSN with energy. The sensor(s) of the WPSN may transmit data by modulating the incident signal from a power source by switching its antenna impedance.

One or more measurements received from a load sensing assembly may be used to make determinations of the condition of a spinal implant and/or treatment of a spinal disorder. For instance, proper placement of a longitudinal member, set screw and/or anchoring member may result in an acceptable range of force measurements collected by a strain gauge of a load sensing assembly. Measurements outside of this range may indicate a problem with the placement or positioning of a longitudinal member, set screw and/or anchoring member such as, for example, loosening of a set screw and/or anchoring member, longitudinal member failure, construct failure, yield or fracture/breakage, improper torque, breakage of the bone segment or portion, the occurrence of fusion or amount of fusion, and/or the like.

One or more tools or instruments may include a reader which may be used to gather information from one or more integrated circuit during or in connection with a procedure. For instance, a torque tool may be used to loosen or tighten a set screw. A torque tool may include a reader, or may be in communication with a reader, such that a user of the torque tool is able to obtain, in substantially real time, one or more measurements relating to the set screw and longitudinal rod placement that are measured by a strain gauge of a load sensing assembly of the set screw via the tool. For instance, as a user is applying torque to a set screw, the user may see one or more force measurements between the set screw and the longitudinal member in order to determine that the positioning of the set screw and/or longitudinal member is correct and that the proper force is being maintained. In certain embodiments, a tool or instrument may include a display device on which one or more measurements may be displayed. In other embodiments, a tool or instrument may be in communication with a display device, and may transmit one or more measurements for display on the display device via a communications network.

In some embodiments, an electronic device, such as a reader or an electronic device in communication with a reader, may compare one or more measurements obtained from an integrated circuit to one or more acceptable value ranges. If one or more of the measurements are outside of an applicable value range, the electronic device may cause a notification to be made. For instance, an electronic device may generate an alert for a user, and cause the alert to be displayed to the user via a display device. Alternatively, an electronic device may send an alert to a user such as via an email message, a text message or otherwise.

An integrated circuit of a load sensing assembly may store a unique identifier associated with the component to which the load sensing assembly corresponds. For instance, an integrated circuit of a load sensing assembly for a set screw may store a unique identifier associated with the set screw. Similarly, an integrated circuit of a load sensing assembly for an anchoring member may store a unique identifier associated with the anchoring member. The integrated circuit may transmit the unique identifier to an electronic device. For instance, when a reader interrogates an integrated circuit, the integrated circuit may transmit a unique identifier for a component that is stored by the integrated circuit to the reader.

Having access to a unique identifier for a component may help a user ascertain whether the measurements that are being obtained are associated with the component of interest. Also, having access to a unique identifier for a component may help a user take inventory of one or more components. For instance, after spinal surgery, a physician or other health care professional may use a reader to confirm that all of the set screws and anchoring members allocated for the procedure have been used and are positioned in a patient.

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. A load sensing assembly for a spinal implant, the load sensing assembly comprising:
a set screw extending in a longitudinal direction from a first end to a second end and having an outside surface comprising a thread pattern and an inside surface comprising a driving feature, the set screw further comprising a central opening that extends in the longitudinal direction from the first end of the set screw toward the second end of the set screw, wherein the thread pattern of the set screw is configured to engage with an anchoring member supporting a longitudinal rod;
an antenna positioned within the central opening;
an integrated circuit in communication with the antenna, wherein the integrated circuit is positioned within the central opening of the set screw; and
a strain gauge in connection with the integrated circuit, wherein the strain gauge is located within the central opening of the set screw in proximity to the second end of the set screw and is configured to measure a localized force between the second end of the set screw and the longitudinal rod when the second end contacts the longitudinal rod.

2. The load sensing assembly of claim 1, wherein the set screw comprises a breakoff portion.

3. The load sensing assembly of claim 1, further comprising an electronics component, wherein the electronics component comprises a top surface, a bottom surface, and one or more electrical circuits.

4. The load sensing assembly of claim 3, wherein the integrated circuit is positioned on the top surface of the electronics component.

5. The load sensing assembly of claim 3, wherein the strain gauge is operably connected to the bottom surface of the electronics component.

6. The load sensing assembly of claim 1, wherein the integrated circuit comprises memory, wherein the integrated circuit is configured to:
store one or more measurements made by the strain gauge in the memory; and transmit the one or more measurements to a reader when the reader is in proximity to the integrated circuit.

7. The load sensing assembly of claim 1, wherein the integrated circuit comprises memory, wherein the integrated circuit is configured to:

store a unique identifier associated with the set screw in the memory; and transmit the unique identifier to a reader when the reader is in proximity to the integrated circuit.

8. The load sensing assembly of claim 1, further comprising an anchoring member comprising a channel that is configured to receive the longitudinal rod and a second strain gauge located within the channel, wherein the second strain gauge is configured to measure a localized force between the anchoring member and the longitudinal rod.

9. The load sensing assembly of claim 1, wherein the integrated circuit comprises one or more of the following:
   radio frequency identification (RFID) chip; or
   near-field communication (NFC) chip.

10. The load sensing assembly of claim 1, wherein the central opening comprises a circular opening defined by a consistent internal diameter.

11. A load sensing assembly for a spinal implant, the load sensing assembly comprising:
   a set screw extending in a longitudinal direction from a first end to a second end and having an outside surface comprising a thread pattern and an inside surface comprising a driving feature, the set screw further comprising a central opening that is coaxially aligned with the driving feature and extends in the longitudinal direction from the first end of the set screw to the second end of the set screw, wherein the thread pattern of the set screw is configured to engage with an anchoring member supporting a longitudinal rod while the second end of the set screw directly contacts the longitudinal rod;
   an antenna;
   an electronics component comprising one or more electrical circuits, wherein the electronics component is operably connected to the antenna;
   an integrated circuit operably connected to at least a portion of the electronics component; and
   a strain gauge in communication with the integrated circuit, wherein the strain gauge is located within the central opening of the set screw in proximity to the second end of the set screw and is configured to measure a localized force between the second end of the set screw and the longitudinal rod.

12. The load sensing assembly of claim 11, wherein the electronics component is operably connected to the antenna via a connecting member having a longitudinal axis that extends in a perpendicular direction with respect to the antenna.

13. The load sensing assembly of claim 11, wherein:
   the antenna comprises a radio frequency identification coil,
   the antenna is configured to circumferentially surround at least a portion of the set screw or a pedicle screw.

14. The load sensing assembly of claim 11, wherein at least a portion of the antenna is positioned in a the central opening of the set screw.

15. The load sensing assembly of claim 11, wherein the integrated circuit comprises memory, wherein the integrated circuit is configured to:
   store one or more measurements made by the strain gauge in the memory; and transmit the one or more measurements to a reader when the reader is in proximity to the integrated circuit.

16. The load sensing assembly of claim 11, wherein the integrated circuit comprises memory, wherein the integrated circuit is configured to:
   store a unique identifier associated with the implant in the memory; and
   transmit the unique identifier to a reader when the reader is in proximity to the integrated circuit.

* * * * *